(12) United States Patent
Moriyasu (10) Patent No.: US 9,662,077 B2
(45) Date of Patent: May 30, 2017

(54) PHOTON-COUNTING X-RAY CT APPARATUS AND PHOTON-COUNTING IMAGING METHOD

(71) Applicant: Toshiba Medical Systems Corporation, Otawara-shi (JP)

(72) Inventor: Kenta Moriyasu, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 9 days.

(21) Appl. No.: 14/741,872

(22) Filed: Jun. 17, 2015

(65) Prior Publication Data

US 2015/0374317 A1    Dec. 31, 2015

(30) Foreign Application Priority Data

Jun. 30, 2014    (JP) .................................. 2014-134975

(51) Int. Cl.
| | | |
|---|---|---|
| *A61B 6/00* | (2006.01) | |
| *A61B 6/03* | (2006.01) | |
| *G01T 1/20* | (2006.01) | |
| *G01T 1/29* | (2006.01) | |

(52) U.S. Cl.
CPC ............ *A61B 6/4241* (2013.01); *A61B 6/032* (2013.01); *A61B 6/482* (2013.01); *A61B 6/5205* (2013.01); *G01T 1/2018* (2013.01); *G01T 1/2985* (2013.01)

(58) Field of Classification Search
USPC ....................................................... 378/19, 5
See application file for complete search history.

(56) References Cited

U.S. PATENT DOCUMENTS

| | | | | |
|---|---|---|---|---|
| 5,285,489 A | * | 2/1994 | Ohtsuchi .................. | H05G 1/26 250/505.1 |
| 6,895,077 B2 | * | 5/2005 | Karellas ................. | A61B 6/481 250/370.09 |
| 9,256,938 B2 | * | 2/2016 | Petschke ............... | G06T 7/0012 |

FOREIGN PATENT DOCUMENTS

JP    2005-253815    9/2005

* cited by examiner

*Primary Examiner* — Phillip A Johnston
(74) *Attorney, Agent, or Firm* — Oblon, McClelland, Maier & Neustadt, L.L.P.

(57) ABSTRACT

A photon-counting X-ray CT apparatus in an embodiment includes an X-ray tube, an X-ray detector, correction circuitry, and processing circuitry. The X-ray tube is configured to irradiate a subject with X-rays. The X-ray detector is configured to include an X-ray detection element that detects photons of the X-rays that the X-ray tube emits. The correction circuitry is configured to correct a count value observed by the X-ray detection element in each of a plurality of energy bins, based on at least one of the probability of escape in the X-ray detection element and the probability of crosstalk in the X-ray detection element. The processing circuitry is configured to generate a reconstruction image, based on the count values corrected by the correction circuitry.

20 Claims, 7 Drawing Sheets

| ENERGY BIN | ENERGY BIN E1 (0 keV TO 30 keV) | ENERGY BIN E2 (30 keV TO 60 keV) | ENERGY BIN E3 (60 keV TO 90 keV) |
|---|---|---|---|
| TRUE COUNT VALUE | 5 | 10 | 5 |
| COUNT VALUE BY ESCAPE | 0 | 2 (20 keV) | 1 (50 keV) |
| COUNT VALUE BY CROSSTALK | 2 | 1 | 0 |
| OBSERVED COUNT VALUE | 9 | 10 | 4 |

| | | CHANNEL DIRECTION (ROW DIRECTION) | | | | |
|---|---|---|---|---|---|---|
| | | A | B | C | D | E |
| SLICE DIRECTION (COLUMN DIRECTION) | 1 | 0.0001 | 0.005 | 0.01 | 0.005 | 0.0001 |
| | 2 | 0.005 | 0.05 | 0.10 | 0.05 | 0.005 |
| | 3 | 0.01 | 0.10 | 0 | 0.10 | 0.01 |
| | 4 | 0.005 | 0.05 | 0.10 | 0.05 | 0.005 |
| | 5 | 0.0001 | 0.005 | 0.01 | 0.005 | 0.0001 |

FIG.8

PHOTON-COUNTING X-RAY CT APPARATUS AND PHOTON-COUNTING IMAGING METHOD

CROSS-REFERENCE TO RELATED APPLICATIONS

This application is based upon and claims the benefit of priority from Japanese Patent Application No. 2014-134975, filed on Jun. 30, 2014, the entire contents of all of which are incorporated herein by reference.

FIELD

An embodiment described herein relates generally to a photon-counting X-ray CT apparatus and a photon-counting imaging method.

BACKGROUND

The development of photon-counting X-ray CT apparatuses is now being advanced. In a photon-counting X-ray CT apparatus, a sufficiently large count value of photons of X-rays is not obtainable due to the limitations of an X-ray detector. Consequently, there are cases in which the photon-counting X-ray CT apparatus receives the influence of statistical noise.

In the X-ray detector installed in the photon-counting X-ray CT apparatus, there are cases in which a photon is counted in an energy bin in which it should not be counted originally by escape. The escape is a phenomenon in which a photon that entered one of a plurality of X-ray detection elements of the X-ray detector gives to the entered X-ray detection element only a part of energy it has at the time of entering, is counted in an energy bin other than an energy bin including the energy it has at the time of entering, and escapes from the X-ray detector without interacting with other X-ray detection elements.

Furthermore, in the X-ray detector installed in the photon-counting X-ray CT apparatus, there are cases in which a photon is counted by an X-ray detection element by which it should not be counted originally by crosstalk. The crosstalk is a phenomenon in which a photon that entered one of a plurality of X-ray detection elements of the X-ray detector is scattered by the entered X-ray detection element, enters other X-ray detection elements, and is counted by the other X-ray detection elements.

Because of the phenomena described above, there have been cases in which the photon-counting X-ray CT apparatus is unable to obtain low-noise data.

DETAILED DESCRIPTION

A photon-counting X-ray CT apparatus in an embodiment includes an X-ray tube, an X-ray detector, correction circuitry, and processing circuitry. The X-ray tube is configured to irradiate a subject with X-rays. The X-ray detector is configured to include an X-ray detection element that detects photons of the X-rays that the X-ray tube emits. The correction circuitry is configured to correct a count value observed by the X-ray detection element in each of a plurality of energy bins, based on at least one of the probability of escape in the X-ray detection element and the probability of crosstalk in the X-ray detection element. The processing circuitry is configured to generate a reconstruction image, based on the count values corrected by the correction circuitry.

With reference to the accompanying drawings, the following describes a photon-counting X-ray CT apparatus and a photon-counting imaging method according to an embodiment.

Embodiment

Figure 1:
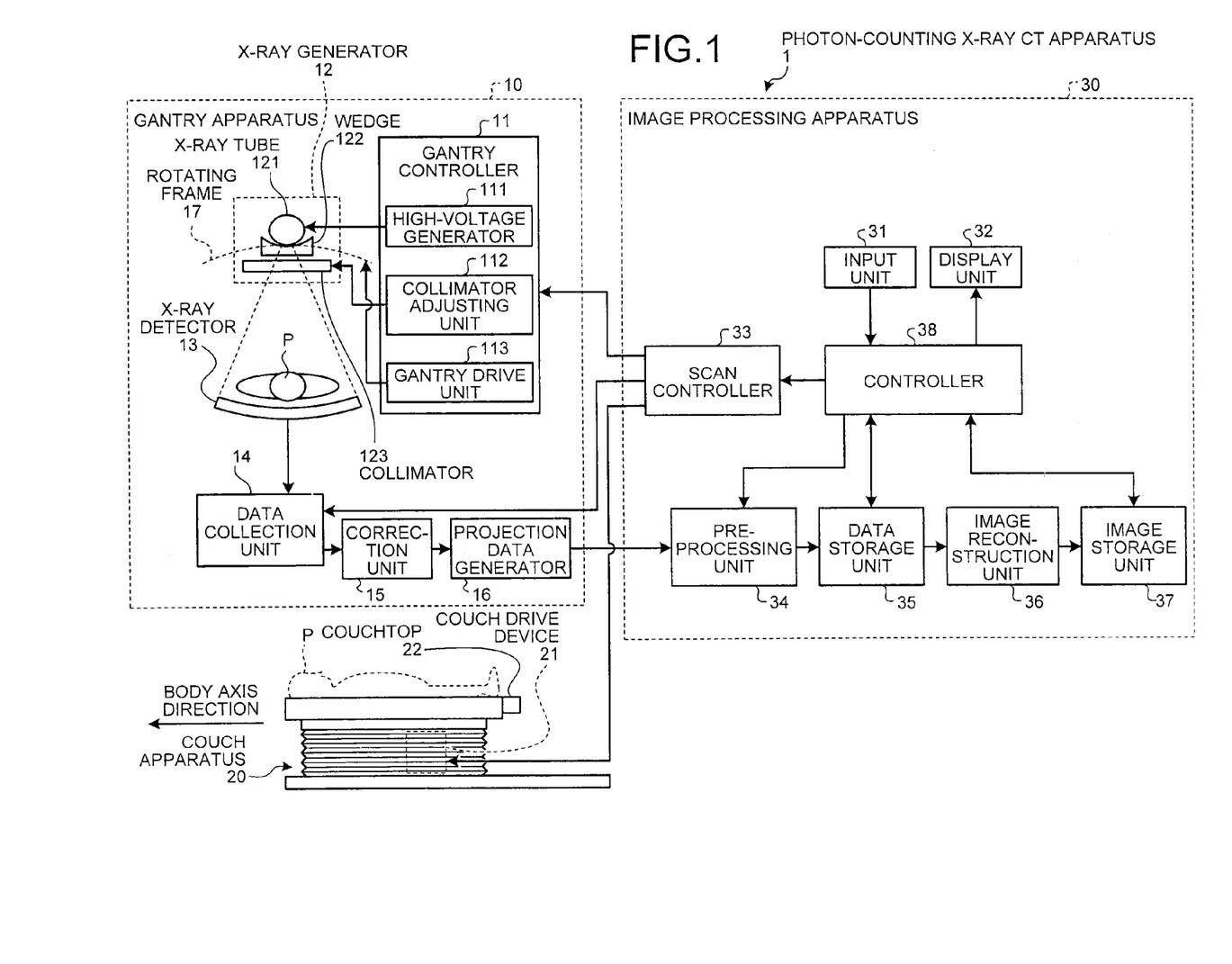
FIG. 1 is a block diagram illustrating one example of the configuration of a photon-counting X-ray CT apparatus according to an embodiment.

With reference to FIG. 1, the configuration of a photon-counting X-ray CT apparatus 1 in the embodiment will be described first. FIG. 1 is a block diagram illustrating one example of the configuration of the photon-counting X-ray CT apparatus 1 in the embodiment. The photon-counting X-ray CT apparatus 1, as illustrated in FIG. 1, includes a gantry apparatus 10, a couch apparatus 20, and an image processing apparatus 30. Note that the configuration of the photon-counting X-ray CT apparatus 1 is not limited to the following configuration.

The gantry apparatus 10 irradiates a subject P with X-rays, and collects projection data, which will be described later. The gantry apparatus 10 includes a gantry controller 11, an X-ray generator 12, an X-ray detector 13, a data collection unit 14, a correction unit 15, a projection data generator 16, and a rotating frame 17.

The gantry controller 11 controls, under the control of a scan controller 33 described later, the operations of the X-ray generator 12 and the rotating frame 17. The gantry controller 11 includes a high-voltage generator 111, a collimator adjusting unit 112, and a gantry drive unit 113. The high-voltage generator 111 supplies a tube voltage to an X-ray tube 121 described later. The collimator adjusting unit 112, by adjusting the position and degree of aperture of a collimator 123, adjusts the irradiation range of the X-rays with which the X-ray generator 12 irradiates the subject P. For example, the collimator adjusting unit 112, by adjusting the aperture of the collimator 123, adjusts the irradiation range of the X-rays, more specifically, the fan angle and cone angle of the X-rays. The gantry drive unit 113, by rotationally driving the rotating frame 17, rotates the X-ray generator 12 and the X-ray detector 13 in a circular path centered on the subject P.

The X-ray generator 12 generates X-rays with which the subject P is irradiated. The X-ray generator 12 includes the X-ray tube 121, a wedge 122, and the collimator 123. The X-ray tube 121 generates beam-shaped X-rays with which the subject P is irradiated, by the tube voltage supplied from the high-voltage generator 111. The X-ray tube 121 is a vacuum tube that generates the beam-shaped X-rays having an expanse in a circular cone and pyramid shape along the direction of body axis of the subject P. The beam-shaped X-rays are also referred to as a cone beam. The X-ray tube 121 irradiates the subject P with the cone beam along with the rotation of the rotating frame 17. The wedge 122 is an X-ray filter to adjust the X-ray dosage of the X-rays emitted from the X-ray tube 121. The collimator 123 is a slit to narrow down the irradiation range of the X-rays for which the X-ray dosage has been adjusted by the wedge 122, by the control of the collimator adjusting unit 112.

The X-ray detector 13 includes X-ray detection elements that detect photons of the X-rays that the X-ray tube 121 irradiates. Specifically, the X-ray detector 13 is a multi-array detector installed with a plurality of X-ray detection elements arrayed in a channel direction and a slice direction. The channel direction is the circumferential direction of the rotating frame 17 and the slice direction is the body axis direction of the subject P. The X-ray detection elements each include a scintillator, a photodiode, and a detection circuit. The X-ray detection element converts each photon of incident X-rays into light one by one by the scintillator, and converts the light into an electrical charge by the photodiode. The electrical charge is converted into a pulsed electrical signal by the detection circuit and is output to the data collection unit 14, which will be described later. The X-ray detector 13 provided with X-ray detection elements that include scintillators and photodiodes is referred to as an indirect conversion detector. The embodiment will be exemplified with the indirect conversion detector primarily.

The X-ray detector 13 may be a direct conversion detector. The direct conversion detector is a detector that converts the photons, which entered the X-ray detection elements, into electrical charges directly. The electrical charges output from the X-ray detection elements are output by at least one of the running of electrons caused by the incident photons toward a collecting electrode of positive electric potential and the running of holes caused by the incident photons toward a collecting electrode of negative electric potential. In the case of a direct conversion detector, the X-ray detection elements are of cadmium telluride (CdTe) based semiconductor elements, for example.

The data collection unit 14 collects, based on an electrical signal the X-ray detection elements of the X-ray detector 13 output, count data that is the data in which the position of the X-ray tube 121, positions of the X-ray detection elements, and observed count values of incident photons are associated with one another, for each of a plurality of energy bins defined on the energy distribution of the X-rays that the X-ray tube 121 emits and for each of a plurality of X-ray detection elements. The position of the X-ray tube 121 is referred to as a view. Because the energy of the photons that caused an output of an electrical signal can be measured by performing arithmetic processes based on the waveform of the pulsed electrical signal, the data collection unit 14 can collect the count data for each energy bin. The data collection unit 14 can observe and collect the count value of the photons incident on each of the X-ray detection elements by counting the number of electrical signals that the X-ray detection elements output. The data collection unit 14 transmits the collected count data to the correction unit 15. The data collection unit 14 is also referred to as a data acquisition system (DAS).

The correction unit 15 corrects a count value observed by an X-ray detection element in each of a plurality of energy bins, based on at least one of the probability of escape in the X-ray detection element and the probability of crosstalk in the X-ray detection element. The correction unit 15 corrects the count value for each of the X-ray detection elements. The detail of the method of correcting the count value observed by the X-ray detection element by the correction unit 15 will be described later. The correction unit 15 transmits the corrected count data to the projection data generator 16.

The projection data generator 16 generates projection data based on the count values observed by the X-ray detection elements included in the count data. Because the count data is collected for each of the energy bins defined on the energy distribution of the X-rays that the X-ray tube 121 emits, the same number of pieces of projection data as the number of the energy bins is generated. The count values that the projection data generator 16 uses for the generation of projection data are the count values that have been corrected by the correction unit 15. The count value of photons is represented as a luminance value of each point of the projection data. The count value of photons may be a value per unit time. The projection data generator 16 can also generate other projection data as necessary by adding the luminance values of respective points of a plurality of pieces of projection data. The projection data generator 16 transmits the generated projection data to the image processing apparatus 30. The projection data generator 16 may be included in the image processing apparatus 30.

The rotating frame 17 is an annular frame that supports the X-ray generator 12 and the X-ray detector 13 so as to face each other interposing the subject P. The rotating frame 17 is driven by the gantry drive unit 113 and rotates in a circular path centered on the subject P at high velocities.

The couch apparatus 20 includes a couch drive device 21 and a couchtop 22, and the subject P is placed thereon. The couch drive device 21, under the control of the scan controller 33, which will be described later, moves the subject P in the rotating frame 17 by moving the couchtop 22, on which the subject P is placed, in the body axis direction. The gantry apparatus 10 performs a helical scan in which the subject P is scanned in a spiral manner by rotating the rotating frame 17 while moving the couchtop 22, for example. Alternatively, the gantry apparatus 10 performs a conventional scan in which the subject P is scanned in a circular path by rotating the rotating frame 17 while the position of the subject P is fixed after moving the couchtop 22. Alternatively, the gantry apparatus 10 performs a step-and-shoot method in which the conventional scan is performed at a plurality of scan areas by moving the position of the couchtop 22 at regular intervals.

The image processing apparatus 30 receives the operation of the photon-counting X-ray CT apparatus 1 by a user and performs a variety of image processing such as reconstruction processing of projection data collected by the gantry apparatus 10. The image processing apparatus 30 includes an input unit 31, a display unit 32, the scan controller 33, a preprocessing unit 34, a data storage unit 35, an image reconstruction unit 36, an image storage unit 37, and a controller 38.

The input unit 31 is a mouse, a keyboard, and others used by the user of the photon-counting X-ray CT apparatus 1 to input various instructions and various settings. The input unit 31 transfers the information on the instructions and settings received from the user to the controller 38. The display unit 32 is a monitor that is referred to by the user. The display unit 32 displays the result of a variety of image processing, and graphical user interfaces (GUIs) to receive various settings from the user via the input unit 31, for example.

The scan controller 33, under the control of the controller 38, controls the operations of the gantry controller 11, the data collection unit 14, and the couch drive device 21. Specifically, when photon-counting CT imaging is performed, the scan controller 33, by controlling the gantry controller 11, rotates the rotating frame 17, makes the X-ray tube 121 emit X-rays, and adjusts the aperture and position of the collimator 123. The scan controller 33, under the control of the controller 38, further controls the data collection unit 14. The scan controller 33, under the control of the controller 38, by further controlling the couch drive device 21, moves the couchtop 22 at the time of imaging the subject P.

The preprocessing unit 34 performs correction processing on the projection data generated by the projection data generator 16. The correction processing is logarithmic conversion, offset correction, sensitivity correction, beam hardening correction, and scattered ray correction, for example. The preprocessing unit 34 stores the projection data on which the correction processing has been performed in the data storage unit 35. The projection data on which the correction processing has been performed by the preprocessing unit 34 is also referred to as raw data.

The data storage unit 35 stores therein the raw data, that is, the projection data on which the correction processing has been performed by the preprocessing unit 34. The image reconstruction unit 36 reconstructs the projection data stored in the data storage unit 35 and generates a reconstruction image. That is, the image reconstruction unit 36 generates the reconstruction image, based on the count values corrected by the correction unit 15. The reconstruction method is back-projection processing and a successive approximation method, for example. The back-projection processing includes a filtered back-projection (FBP) method, for example. The image storage unit 37 stores therein the reconstruction image generated by the image reconstruction unit 36.

The controller 38 controls the photon-counting X-ray CT apparatus 1 by controlling the operations of the gantry apparatus 10, the couch apparatus 20, and the image processing apparatus 30. The controller 38 controls the scan controller 33 to perform scan and collects projection data from the gantry apparatus 10. The controller 38 controls the preprocessing unit 34 to perform the correction processing described above on the projection data. The controller 38 executes control such that the projection data stored in the data storage unit 35 and the image data stored in the image storage unit 37 are displayed on the display unit 32.

The data storage unit 35 and the image storage unit 37 in the foregoing can be implemented with a semiconductor memory device, a hard disk, and an optical disc, for example. The semiconductor memory device is a random access memory (RAM) and a flash memory, for example. The scan controller 33, the preprocessing unit 34, the image reconstruction unit 36, and the controller 38 in the foregoing can be implemented with an integrated circuit and an electronic circuit. The integrated circuit is an application specific integrated circuit (ASIC) and a field programmable gate array (FPGA), for example. The electronic circuit is a central processing unit (CPU) and a micro processing unit (MPU), for example.

Figure 2:
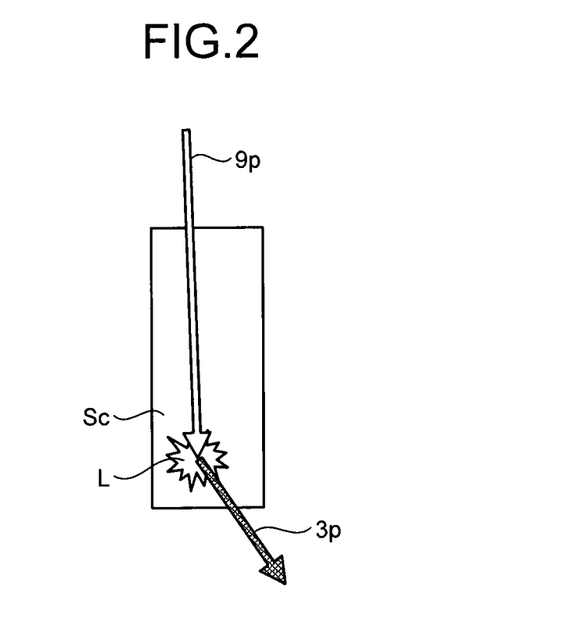
FIG. 2 is a diagram for explaining one example of escape.
Figure 3:
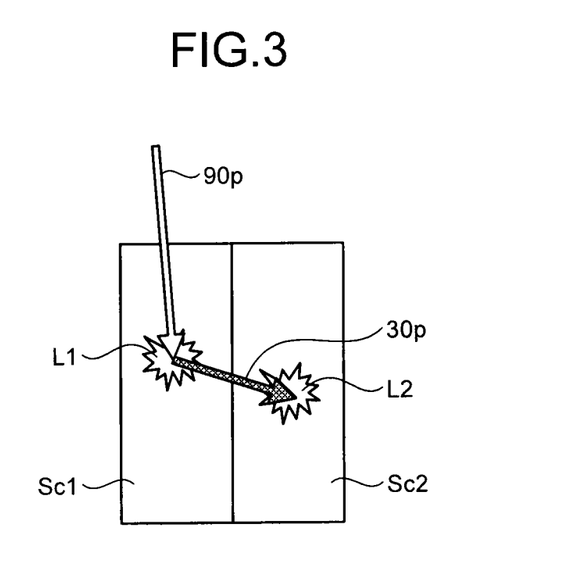
FIG. 3 is a diagram for explaining one example of crosstalk.

Next, with reference to FIGS. 2 and 3, the escape and crosstalk will be described. FIG. 2 is a diagram for explaining one example of the escape. FIG. 3 is a diagram for explaining one example of the crosstalk.

The escape is a phenomenon in which a photon that entered one of a plurality of X-ray detection elements of an X-ray detector gives to the entered X-ray detection element only a part of energy it has at the time of entering, is counted at an energy bin other than the energy bin including the energy it has at the time of entering, and escapes from the X-ray detector without interacting with other X-ray detection elements.

The escape means a phenomenon as illustrated in FIG. 2, for example. As indicated by an arrow 9p, a photon having the energy of 90 keV enters a scintillator Sc. The photon that has the energy of 90 keV gives only the energy of 60 keV to the scintillator Sc out of the energy of 90 keV and turns into a photon having the energy of 30 keV. As indicated by an arrow 3p, the photon having the energy of 30 keV escapes from the X-ray detector without entering other scintillators. Thus, in the scintillator Sc, light L corresponding to the energy of 60 keV is emitted and one photon is counted in an energy bin including 60 keV. Consequently, the photon that should be counted originally in an energy bin including 90 keV of the scintillator Sc ends up not being counted in the energy bin including 90 keV of the scintillator Sc by the escape.

Note that the escape includes the phenomenon in which a photon that enters a scintillator passes through the entered scintillator and is not counted in any of the energy bins.

The crosstalk is a phenomenon in which a photon that entered one of a plurality of X-ray detection elements of an X-ray detector is scattered by the entered X-ray detection element, enters other X-ray detection elements, and is counted by the other X-ray detection elements.

The crosstalk means a phenomenon as illustrated in FIG. 3, for example. As indicated by an arrow 90p, a photon having the energy of 90 keV enters a scintillator Sc1. The photon that has the energy of 90 keV gives only the energy of 60 keV to the scintillator Sc1 out of the energy of 90 keV and turns into a photon having the energy of 30 keV. Thus, in the scintillator Sc1, light L1 corresponding to the energy of 60 keV is emitted and one photon is counted in an energy bin including 60 keV.

As indicated by an arrow 30p, the photon having the energy of 30 keV is scattered by the scintillator Sc1 and enters a scintillator Sc2. The photon that has the energy of 30 keV gives the energy of 30 keV to the scintillator Sc2. Thus, in the scintillator Sc2, light L2 corresponding to the energy of 30 keV is emitted and one photon is counted in an energy bin including 30 keV. Consequently, the photon that should be counted originally in an energy bin including 90 keV of the scintillator Sc1 ends up being counted in the energy bin including 60 keV of the scintillator Sc1 and in the energy bin including 30 keV of the scintillator Sc2, by the crosstalk.

Figure 4:
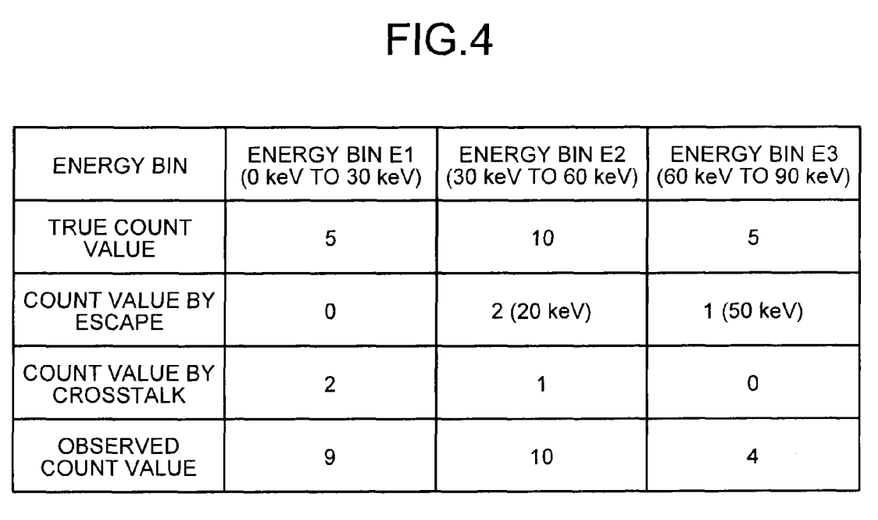
FIG. 4 is a table illustrating one example of count values in respective energy bins of one scintillator.

Next, with reference to FIG. 4, one example of count values in respective energy bins of one scintillator will be described. FIG. 4 is a table illustrating one example of count values in respective energy bins of one scintillator.

As illustrated in FIG. 4, considered is a situation in which three of an energy bin E1, an energy bin E2, and an energy bin E3 are defined on the energy distribution of X-rays with which the subject P is irradiated. The energy bin E1 is in the range of 0 to 30 keV. The energy bin E2 is in the range of 30 to 60 keV. The energy bin E3 is in the range of 60 to 90 keV.

As illustrated in FIG. 4, the true count values are "5" in the energy bin E1, "10" in the energy bin E2, and "5" in the energy bin E3. By escape and crosstalk, however, the observed count values are "9" in the energy bin E1, "10" in the energy bin E2, and "4" in the energy bin E3. The following describes the respective count values in the energy bin E1, the energy bin E2, and the energy bin E3.

The count value in the energy bin E1 will be described first.

In the energy bin E1, the count value by crosstalk is "2." This count value is the counted photons that entered a focused scintillator from the scintillators other than the focused scintillator by crosstalk. Consequently, in the energy bin E1, the subtraction of the count value "2" by crosstalk from the observed count value "9" is necessary.

In the energy bin E2, the count value by escape is "2 (20 keV)." This count value is attributable to two photons that had energy that is included in the energy bin E2, entered the focused scintillator, gave only the energy of 20 keV to the focused scintillator, and escaped from an X-ray detector without entering the other scintillators. Thus, in the energy bin E1, the count value "2 (20 keV)" by escape is counted. Consequently, in the energy bin E1, the subtraction of the count value "2 (20 keV)" by escape from the observed count value "9" is necessary.

Thus, it can tell that the true count value "5" in the energy bin E1 is equal to the value in which the count value "2" by crosstalk and the count value "2 (20 keV)" by escape are subtracted from the observed count value "9."

Next, the count value in the energy bin E2 will be described.

In the energy bin E2, the count value by crosstalk is "1." This count value is the counted photon that entered the focused scintillator from the scintillator other than the focused scintillator by crosstalk. Consequently, in the energy bin E2, the subtraction of the count value "1" by crosstalk from the observed count value "10" is necessary.

In the energy bin E3, the count value by escape is "1 (50 keV)." This count value is attributable to one photon that had energy that is included in the energy bin E3, entered the focused scintillator, gave only the energy of 50 keV to the focused scintillator, and escaped from the X-ray detector without entering the other scintillators. Thus, in the energy bin E2, the count value "1 (50 keV)" by escape is counted. Consequently, in the energy bin E2, the subtraction of the count value "1 (50 keV)" by escape from the observed count value "10" is necessary.

Furthermore, in the energy bin E2, the count value by escape is "2 (20 keV)." This count value is attributable to two photons that had energy that is included in the energy bin E2, entered the focused scintillator, gave only the energy of 20 keV to the focused scintillator, and escaped from the X-ray detector without entering the other scintillators. Thus, in the energy bin E2, the count value "2 (20 keV)" by escape is not counted. Consequently, in the energy bin E2, the addition of the count value "2 (20 keV)" by escape to the observed count value "10" is necessary.

Thus, it can tell that the true count value "10" in the energy bin E2 is equal to the value in which the count value "1" by crosstalk and the count value "1 (50 keV)" by escape are subtracted from the observed count value "10" and to which the count value "2 (20 keV)" by escape is added.

Finally, the count value in the energy bin E3 will be described.

In the energy bin E3, the count value by escape is "1 (50 keV)." This count value is attributable to one photon that had energy that is included in the energy bin E3, entered the focused scintillator, gave only the energy of 50 keV to the focused scintillator, and escaped from the X-ray detector without entering the other scintillators. Thus, in the energy bin E3, the count value "1 (50 keV)" by escape is not counted. Consequently, in the energy bin E3, the addition of the count value "1 (50 keV)" by escape to the observed count value "10" is necessary.

Thus, it can tell that the true count value "5" in the energy bin E3 is equal to the value in which the count value "1 (50 keV)" by escape is added to the observed count value "4."

As in the foregoing, with reference to FIG. 4, one example of count values in respective energy bins of one scintillator has been described. In practice, the escape and crosstalk occur at a predetermined probability. Thus, the correction unit 15 performs the correction in which a value based on at least one of the probability of escape and the probability of crosstalk is added to or subtracted from an observed count value. Specifically, the correction unit 15 corrects the observed count value by using the following Expression (1).

$$C_C(b,i) = C(b,i) - \Sigma_{b'} \Sigma_j C_C(b',j) \times f(b,b',i,j) + C_C(b,i) \times g(b,i) - \Sigma_{b''} C_C(b,i) \times h(b,b'',i) \quad (1)$$

$C_c$ is a true count value, C is the observed count value, b, b', and b" are indices to distinguish energy bins, i and j are indices to distinguish scintillators. Thus, the left-hand side $C_c(b,i)$ of Expression (1) represents a true count value in the energy bin b of the scintillator i, and the first term $C(b,i)$ on the right-hand side of Expression (1) represents an observed count value in the energy bin b of the scintillator i. $g(b,i)$ and $h(b,b'',i)$ represent the probability of escape. $f(b,b',i,j)$ represents the probability of crosstalk. The following describes the details of $g(b,i)$, $h(b,b'',i)$, and $f(b,b',i,j)$.

The probability of escape includes the probability that a photon that entered an X-ray detection element is not counted in the energy bin including the energy of the photon by escape. Specifically, the probability of escape includes the probability $g(b,i)$ that a photon having energy that is included in the energy bin b and entering the scintillator i is not counted in the energy bin b of the scintillator i by escape. $g(b,i)$ is uniquely determined by the material and shape of the scintillator i, and by the energy of the photon entering the scintillator i.

The probability of escape includes the probability that a photon that entered an X-ray detection element is counted in an energy bin other than the energy bin including the energy of the photon by escape. Specifically, the probability of escape includes the probability $h(b,b'',i)$ that a photon having energy that is included in the energy bin b" and entering the scintillator i is counted in the energy bin b of the scintillator i by escape. $h(b,b'',i)$ is uniquely determined by the material and shape of the scintillator by the energy of the photon entering the scintillator i, and by the energy of the entered photon given to the scintillator i.

The probability of crosstalk is the probability in which a photon that entered an X-ray detection element other than the X-ray detection element, the observed count value of which is corrected, out of a plurality of X-ray detection elements enters the X-ray detection element, the observed count value of which is corrected, by crosstalk and is counted in an energy bin including the energy the photon had at the time of entering the X-ray detection element the observed count value of which is corrected. Specifically, the probability of crosstalk is the probability $f(b,b',i,j)$ that a photon having energy that is included in the energy bin b' and entering the scintillator j enters the scintillator i by crosstalk and is counted in the energy bin b of the scintillator i. $f(b,b',i,j)$ is uniquely determined by the energy of a photon entering the scintillator j, the energy the photon gives to the scintillator j or the energy of the photon entering the scintillator i, the energy the photon gives to the scintillator i, the positional relation between the scintillator i and the scintillator j, and the material and shape of the scintillator i and the scintillator j.

Next, the second term, the third term, and the fourth term on the right-hand side of Expression (1) will be described.

The third term on the right-hand side of Expression (1) is the following Expression (2). The true count value of a photon that had energy that is included in the energy bin b and entered the scintillator i is Cc(b,i). However, the photon that had the energy that is included in the energy bin b and entered the scintillator i is not counted in the energy bin b of the scintillator i at the probability of g(b,i) by escape. Consequently, the correction unit 15 can compensate the count lost due to escape by adding a count value expressed by Expression (2) to the observed count value C(b,i). The third term on the right-hand side of Expression (1) has only the number of energy bins for the scintillator and thus even when it is considered for all of the scintillators that the X-ray detector 13 is provided with, an increase in processing load of the correction unit 15 is limited. Furthermore, when a great number of energy bins are defined on the energy distribution of X-rays emitted by the X-ray tube 121, the processing load can be reduced by assuming a plurality of energy bins as a new single energy bin and applying Expression (2).

$$C_{escape} = C_C(b,i) \times g(b,i) \quad (2)$$

The fourth term on the right-hand side of Expression (1) is the following Expression (3). The true count value of a photon that had energy that is included in the energy bin b and entered the scintillator i is Cc(b,i). However, a photon that had the energy that is included in the energy bin b" and entered the scintillator i ends up being counted in the energy bin b of the scintillator i at the probability of h(b,b",i) along with escape. Furthermore, when a plurality of energy bins other than the energy bin b are defined, this phenomenon occurs on all of the energy bins. Consequently, the correction unit 15 can correct the count by the energy given wrongly along with escape by subtracting a count value expressed by Expression (3) from the observed count value C(b,i).

$$C_{DeffEnergy} = \Sigma_b C_C(b,i) \times h(b,b'',i) \quad (3)$$

The second term on the right-hand side of Expression (1) is the following Expression (4). The true count value of a photon that had energy that is included in the energy bin b' and entered the scintillator j is Cc(b',j). However, a photon that had the energy that is included in the energy bin b' and entered the scintillator j ends up being counted in the energy bin b of the scintillator i at the probability of f(b,b',i,j) by crosstalk. Furthermore, when a plurality of energy bins other than the energy bin b are defined, this phenomenon occurs on all of the energy bins. Moreover, when there are a plurality of scintillators other than the scintillator i, this phenomenon occurs on all of the scintillators. Consequently, the correction unit 15 can correct for the count wrongly counted due to crosstalk by subtracting a count value expressed by Expression (4) from the observed count value C(b,i). Because the second term on the right-hand side of Expression (1) needs to take the sum of all of the energy bins other than the energy bin b and all of the scintillators other than the scintillator i, the processing load of the correction unit 15 becomes heavy. Consequently, it is preferable that the correction unit 15 use a matrix, which will be described later, when calculating the count value expressed by Expression (4).

$$C_{cross} = \Sigma_b \Sigma_j C_C(b',j) \times f(b,b',i,j) \quad (4)$$

In the foregoing, the respective terms of Expression (1) have been explained. On the right-hand side of Expression (1), the true count value Cc(b',j) of a photon that had energy that is included in the energy bin b' and entered the scintillator j is included. Thus, the correction unit 15 cannot solve Expression (1). Consequently, the correction unit 15 applies, to Expression (1), a condition derived from escape and a condition derived from crosstalk.

The condition derived from escape will be described first. A situation will be considered in which a photon that had the energy that is included in the energy bin b" and entered the scintillator i is counted in the energy bin b of the scintillator i by escape. The energy the photon gives to the scintillator i is smaller than the energy the photon had at the time of entering. Thus, the energy bin b in which the photon is counted is to be an energy bin of lower energy than the energy bin b". Consequently, it is derived that the sum of the energy bins other than the energy bin b in Expression (3) only needs to consider the energy bins of higher energy than the energy bin b.

Next, the condition derived from crosstalk will be described. A situation will be considered in which a photon that had the energy that is included in the energy bin b' and entered the scintillator j is counted in the energy bin b of the scintillator i by crosstalk. The energy the photon gives to the scintillator i is smaller than the energy the photon had at the time of entering the scintillator j. Thus, the energy bin b in which the photon is counted is to be an energy bin of lower energy than the energy bin b'. Consequently, it is derived that the sum of the energy bins other than the energy bin b in Expression (4) only needs to consider the energy bins of higher energy than the energy bin b.

The correction unit 15 can derive the following Expression (5) by applying, to Expression (1), the condition derived from escape and the condition derived from crosstalk. In Expression (5), by the condition derived from escape, the fourth term on the right-hand side is to take the sum of only the energy bins of higher energy than the energy bin b. In Expression (5), by the condition derived from crosstalk, the second term on the right-hand side is to take the sum of only the energy bins of higher energy than the energy bin b. The detail of the method of using Expression (5) will be described later.

$$C_C(b,i) = C(b,i) - \Sigma_{b'>b} \Sigma_j C_C(b',j) \times f(b,b',i,j) + C_C(b,i) \times g(b,i) - \Sigma_{b''>b} C_C(b,i) \times h(b,b'',i) \quad (5)$$

Figure 5:
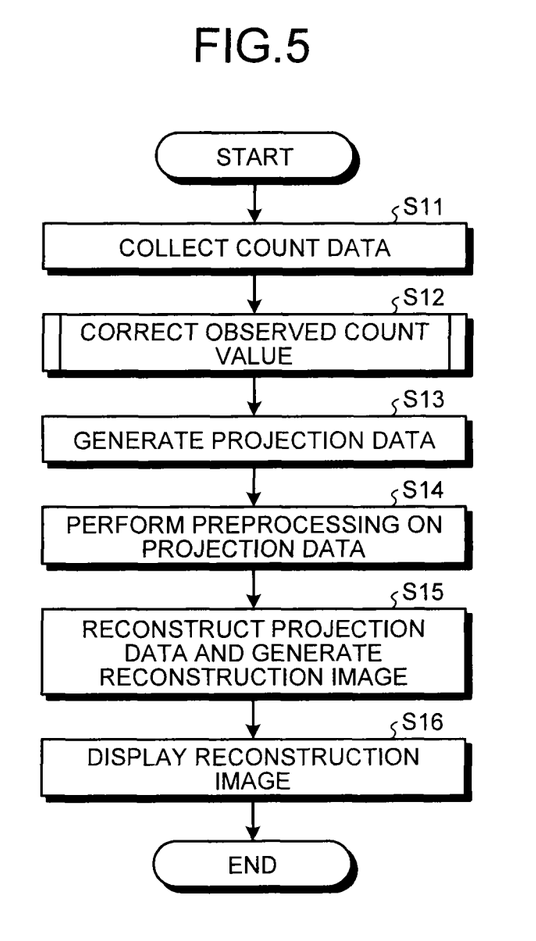
FIG. 5 is a flowchart illustrating one example of processing performed by the photon-counting X-ray CT apparatus in the embodiment.

Next, with reference to FIG. 5, one example of processing performed by the photon-counting X-ray CT apparatus 1 in the embodiment will be described. FIG. 5 is a flowchart illustrating one example of processing performed by the photon-counting X-ray CT apparatus 1 in the embodiment.

As illustrated in FIG. 5, the data collection unit 14 collects count data (Step S11). Specifically, the controller 38 controls the gantry apparatus 10, the couch apparatus 20, and the image processing apparatus 30 so as to perform photon-counting CT imaging, and controls the data collection unit 14 so as to collect the count data.

As illustrated in FIG. 5, the correction unit 15 corrects observed count values included in the count data (Step S12). The details at Step S12 will be described later.

As illustrated in FIG. 5, the projection data generator 16 generates projection data (Step S13). The preprocessing unit 34 performs preprocessing on the projection data (Step S14). The projection data on which the preprocessing has been performed is stored in the data storage unit 35. The image reconstruction unit 36 reconstructs the projection data stored in the data storage unit 35 and generates a reconstruction image (Step S15). The generated reconstruction image is stored in the image storage unit 37. The display unit 32 displays the reconstruction image stored in the image storage unit 37 (Step S16).

Figure 6:
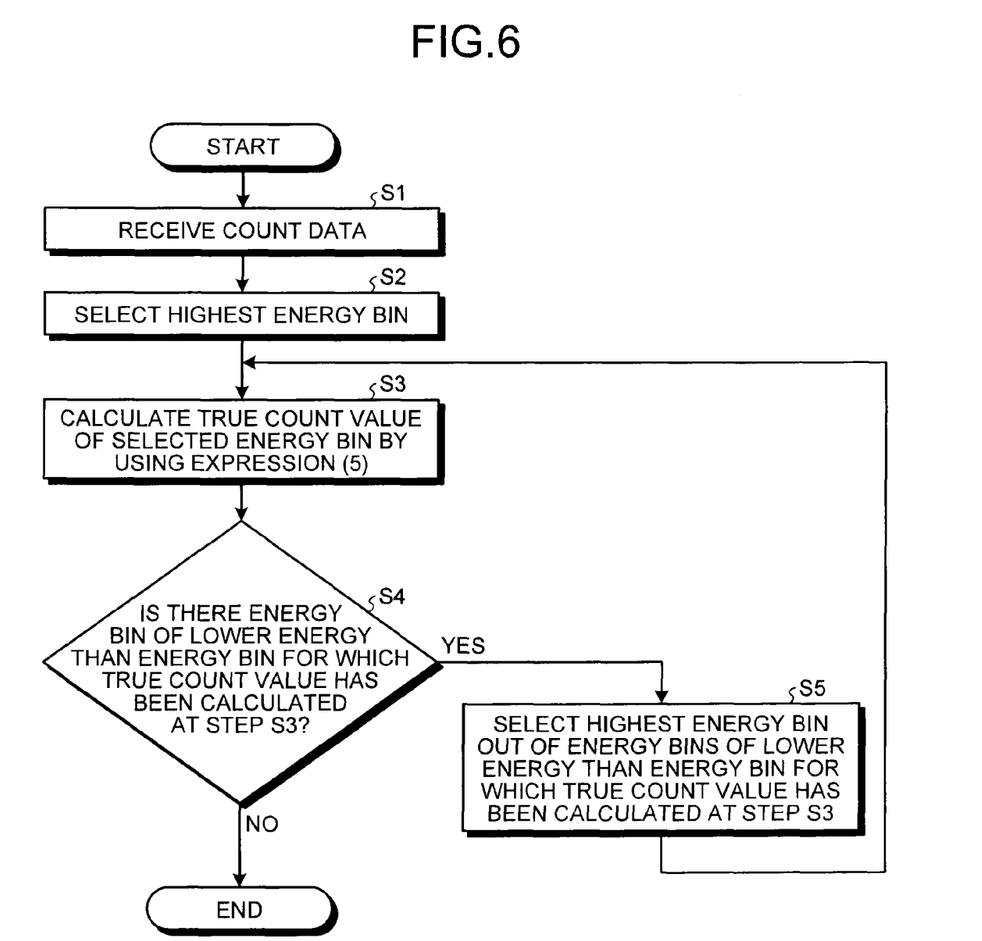
FIG. 6 is a flowchart illustrating one example of the processing performed at Step S12 in FIG. 5 in the embodiment.

Next, with reference to FIG. 6, the details at Step S12 in FIG. 5 will be described. FIG. 6 is a flowchart illustrating one example of the processing performed at Step S12 in FIG. 5 in the embodiment.

The correction unit 15 receives the count data from the data collection unit 14 (Step S1). The correction unit 15 selects a highest energy bin out of a plurality of energy bins defined on the energy distribution of X-rays that the X-ray tube 121 emits (Step S2). The energy bin selected at Step S2 is the energy bin b in Expression (5).

The correction unit 15 calculates a true count value of the selected energy bin by using Expression (5) (Step S3). That is, the correction unit 15 corrects the observed count value $C(b,i)$ by using Expression (2), Expression (3), and Expression (4). When the highest energy bin out of a plurality of energy bins is selected as the energy bin b, the second term and the fourth term on the right-hand side of Expression (5) are zero. Consequently, the correction unit 15 can calculate the true count value of the scintillator i in the energy bin selected at Step S2.

The correction unit 15 determines whether there are any energy bins of lower energy than the energy bin for which the true count value has been calculated at Step S3 (Step S4). If there is no energy bin of lower energy than the energy bin for which the true count value has been calculated at Step S3 (No at Step S4), the correction unit 15 then ends the correction. If there are any energy bins of lower energy than the energy bin for which the true count value has been calculated at Step S3 (Yes at Step S4), the correction unit 15 then advances the processing to Step S5.

The correction unit 15 selects a highest energy bin out of the energy bins of lower energy than the energy bin for which the true count value has been calculated at Step S3 (Step S5). The energy bin selected at Step S5 is the energy bin b in Expression (5). The correction unit 15 then calculates, by using Expression (5) and the true count value calculated at Step S3, a true count value in the energy bin selected at Step S5.

When the energy bin is selected at Step S5 again, the correction unit 15 calculates a true count value in the currently selected energy bin, by using Expression (5), the true count value in the energy bin selected at Step S2, and the true count value in the energy bin previously selected at Step S5.

By the processing illustrated in FIG. 6, the correction unit 15 can correct observed count values in the respective energy bins of the scintillator i in sequence from the energy bin of high energy.

In other words, the -processing performed at Step S12 in FIG. 5 described above is as follows. A plurality of energy bins in the foregoing include a first energy bin that includes first energy and a second energy bin that includes second energy and is lower than the first energy bin. The correction unit 15 then corrects a count value of the first energy bin, and by using the corrected count value, corrects a count value of the second energy bin. The first energy bin corresponds to the energy bin for which the true count value was calculated at Step S3. The second energy bin corresponds to the energy bin of lower energy than the energy bin for which the true count value was calculated at Step S3.

In the foregoing, a situation has been explained in which the correction unit 15 uses Expression (2), Expression (3), and Expression (4) when correcting the observed count values. The correction unit 15 only needs to use at least one of Expression (2), Expression (3), and Expression (4) when correcting the observed count values. Consequently, the correction unit 15 can bring the observed count values in the respective energy bins close to the true count values in the respective energy bins.

Furthermore, when at least one of Expression (2), Expression (3), and Expression (4) are used, the correction unit 15 may weight them. When the probability of escape or the probability of crosstalk varies depending on an observed count value or the like, such a weighting serves as a coefficient to correct the probability of escape or the probability of crosstalk, for example. Moreover, the value of such a weighting may be assumed to be the probability of escape or the probability of crosstalk.

Figure 7:
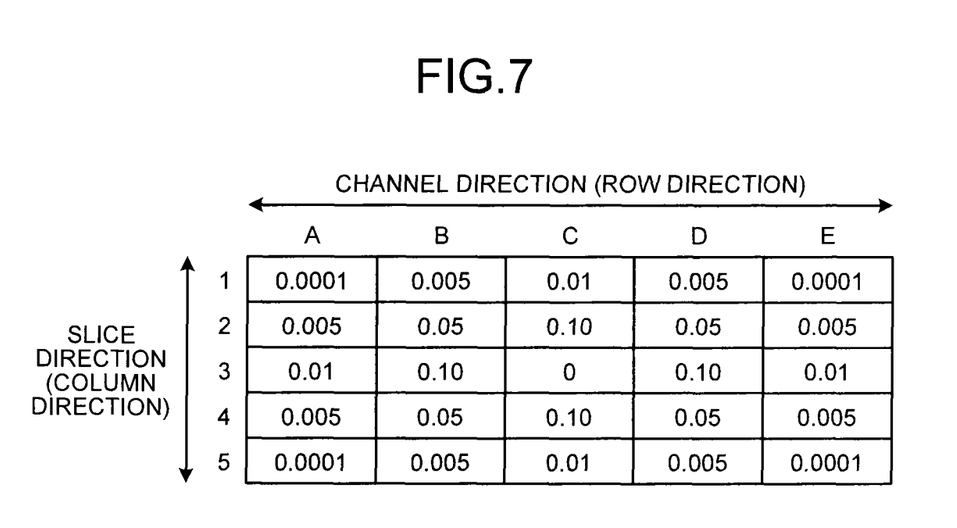
FIG. 7 is a diagram illustrating one example of a matrix that is used when a correction unit corrects an observed count value by using Expression (4) in the embodiment.

Next, with reference to FIG. 7, the method of reducing the load of processing performed by the correction unit 15 will be described. FIG. 7 is a diagram illustrating one example of a matrix used when the correction unit 15 corrects an observed count value by using Expression (4) in the embodiment.

The correction unit 15 uses the result of the probability of crosstalk calculated on at least one of the other X-ray detection elements in advance when correcting an observed count value. Specifically, the correction unit 15 uses a matrix of five rows and five columns illustrated in FIG. 7, for example. The row direction of the matrix is the channel direction of the X-ray detector 13. In FIG. 7, five numerals are given on the left side of the matrix to represent the rows of the matrix. The column direction of the matrix is the slice direction of the X-ray detector 13. In FIG. 7, five alphabets are given on the upper side of the matrix to represent the columns of the matrix. In the following description, each element of the matrix is represented by using these numerals and alphabets.

Each element of the matrix illustrated in FIG. 7 represents the value of the $f(b,b',i,j)$ in a situation in which the energy of a photon entering the scintillator j, the energy that the photon gives to the scintillator j, the energy of the photon entering the scintillator i, and the energy that the photon gives to the scintillator i are fixed at predetermined values. The element in the column C of the third row corresponds to the scintillator i on which a true count value for each energy bin is calculated by using Expression (5), and thus has a value of "0." The elements in the column C of the second row, the column B of the third row, the column D of the third row, and the column C of the fourth row have a value of "0.10." The elements in the column B of the second row, the column D of the second row, the column B of the fourth row, and the column D of the fourth row have a value of "0.05." The elements in the column C of the first row, the column A of the third row, the column E of the third row, and the column C of the fifth row have a value of "0.01." The elements in the column B of the first row, the column D of the first row, the column A of the second row, the column E of the second row, the column A of the fourth row, the column E of the fourth row, the column B of the fifth row, and the column D of the fifth row have a value of "0.005." The elements in the column A of the first row, the column E of the first row, the column A of the fifth row, and the column E of the fifth row have a value of "0.0001."

The correction unit 15 may use a plurality of matrices corresponding to the energy of a photon entering the scintillator j, the energy that the photon gives to the scintillator j, the energy of the photon entering the scintillator i, and the energy that the photon gives to the scintillator i. These matrices are created by actual measurement or simulation, which will be described later.

The correction unit 15 uses the matrix illustrated in FIG. 7 in the following manner when correcting an observed count value Cc(b,i) of a photon, which had energy that is included in the energy bin b and entered the scintillator by using Expression (4). The correction unit 15 assumes the scintillator i to be the element in the column C of the third row of the matrix illustrated in FIG. 7. The correction unit 15 then assumes that the respective scintillators in the X-ray detector 13 within the range of five rows and five columns centered on the scintillator i are the respective elements of the matrix in FIG. 7 other than that of the column C of the third row. The correction unit 15 then uses, as the values of the probability f(b,b',i,j) of the photons that enter the scintillator i from the respective scintillators within the range of five rows and five columns centered on the scintillator i due to crosstalk and are counted in the energy bin b of the scintillator i, the values of the respective elements other than that of the column C of the third row of the matrix illustrated in FIG. 7. Consequently, the correction unit 15 can rapidly correct the observed count value. When there are no scintillators that can be assumed as the elements of the matrix because the scintillator i is located at the four corners of or the end portions of the X-ray detector 13 or at their peripheries, the value of the f(b,b',i,j) of these elements only needs to be assumed to be zero.

The correction unit 15 assumes each of the scintillators of the X-ray detector 13 as the element in the column C of the third row in the matrix illustrated in FIG. 7, and performs the correction described above by using the values of the respective elements other than that of the column C of the third row of the matrix illustrated in FIG. 7 as the value of the f(b,b',i,j). Consequently, the photon-counting X-ray CT apparatus 1 does not need to store the values of the probability f(b,b',i,j) for all of the combinations of the scintillator i and the scintillator j in the X-ray detector 13, and thus can save the storage area. Furthermore, the correction unit 15 does not need to consider all of the combinations of the scintillator i and the scintillator j in the X-ray detector 13, and thus can rapidly correct the observed count value.

The size of the matrix used when the correction unit 15 corrects the observed count value is not particularly limited. Furthermore, the result of the probability of crosstalk calculated on at least one of the other scintillators in advance needs to have only the probability of crosstalk from a scintillator that is in any positional relation with the scintillator the observed count value of which is corrected, as long as all of the scintillators of the X-ray detector 13 are of the same material, size, and shape. When all of the scintillators of the X-ray detector 13 are not of the same material, size, and shape, the difference for that only needs to be reflected on the values of the elements of the matrix. For example, if there is a scintillator for which the length in the direction that X-rays enter is a half the length of the other scintillators, then the probability of crosstalk only needs to be defined lower for that.

The correction unit 15 may use, as the result of the probability of crosstalk calculated on at least one of the other scintillators in advance, the probability of crosstalk of other X-ray detection elements that are in a predetermined positional relation with an X-ray detection element when correcting the observed count value. For example, the correction unit 15 may use a matrix of three rows and three columns that is centered on the X-ray detection element for which the observed count value is corrected. The other X-ray detection elements in a predetermined positional relation with the X-ray detection element for which the observed count value is corrected do not necessarily need to be positioned with respect to the X-ray detection element for which the observed count value is corrected in an isotropic manner.

In the case in which the number of energy bins is increased, the correction unit 15 may reduce the number of other X-ray detection elements used for the result of the probability of crosstalk calculated on at least one of the other X-ray detection elements in advance when correcting an observed count value. Specifically, in the case in which the number of energy bins defined on the energy distribution is increased, the correction unit 15 reduces the size of the matrix used when correcting by using Expression (4). Consequently, the correction unit 15 can offset the increased processing load due to the increase in the number of energy bins, and thus can rapidly correct the observed count value.

The correction unit 15 may use, for the result of the probability of crosstalk calculated on at least one of the other X-ray detection elements in advance, only the other X-ray detection elements for which the probability of crosstalk is equal to or higher than a given threshold, when correcting an observed count value. Specifically, out of the elements of the matrix used when correcting an observed count value by using Expression (4), the correction unit 15 considers only the elements for which the value of the f(b,b',i,j) is equal to or higher than the threshold, and assumes the value of the f(b,b',i,j) of the elements, which are below the threshold, to be zero. Consequently, the processing load is reduced, and thus the correction unit 15 can rapidly correct the observed count value.

In the case in which the speed of correction decreases, the correction unit 15 may reduce the number of other X-ray detection elements used for the result of the probability of crosstalk calculated on at least one of the other X-ray detection elements in advance when correcting an observed count value. For example, in the case in which the user or the controller 38 determines that the speed of correction performed by the correction unit 15 has decreased, the correction unit 15 reduces the size of the matrix used when correcting by using Expression (4). Consequently, the correction unit 15 can reduce the processing load, and thus can rapidly correct the observed count value.

In the foregoing, a situation has been exemplified in which the crosstalk occurs between two X-ray detection elements. However, the crosstalk may occur among X-ray detection elements of three or more, and the correction described above can also be applied to such crosstalk. For example, a situation will be considered in which the crosstalk occurs among four X-ray detection elements. The probability of a photon that has energy that is included in an energy bin $b_3$ and entered a scintillator $j_3$ entering a scintillator $j_2$ and being counted in an energy bin $b_2$ of the scintillator $j_2$, entering a scintillator $j_1$ and being counted in an energy bin $b_1$ of the scintillator $j_1$, and entering a scintillator j and being counted in an energy bin b of the scintillator j by crosstalk is defined as $f(b,b_1,b_2,b_3,i,j_1,j_2,j_3)$. The true count value of the photon that had energy that is included in the energy bin $b_3$ and entered the scintillator $j_3$ is $Cc(b_3,j_3)$. Thus, the correction unit 15 can correct for the counts wrongly counted due to crosstalk, by subtracting, from the observed count value C(b,j), the product of the true count value Cc(b,j) and the $f(b,b_1,b_2,b_3,i,j_1,j_2,j_3)$ that is the sum of all of the energy bins other than the energy bin b and all of the scintillators other than the scintillator i. Also in this case, for the same reason as that in the case of Expression (4), the sum of the energy bins other than the energy bin b only needs to consider the energy bins of higher energy than the energy bin b.

Next, the method of obtaining the values of g(b,i), h(b,b",i), and f(b,b',i,j) included in Expression (1) and Expression (5) will be described. The method of obtaining the values of g(b,i), h(b,b",i), and f(b,b',i,j) includes two of actual measurement and simulation.

The probability of escape is obtainable by actual measurement. The method of obtaining the values of g(b,i) and h(b,b",i) by actual measurement is as follows, for example. The X-rays for which the energy distribution is known are made to enter only one of the X-ray detection elements of the X-ray detector 13. In this case, an observed count value for each energy bin of the X-ray detection element that the X-rays were made to enter differs from a true count value by escape. The true count value, however, can be calculated from the energy distribution of the X-rays that were made to enter one of the X-ray detection elements of the X-ray detector 13. Consequently, from the true count value calculated from the energy distribution of the X-rays that were made to enter one of the X-ray detection elements of the X-ray detector 13 and the observed count value for each energy bin of the X-ray detection element that the X-rays were made to enter, the values of g(b,i) and h(b,b",i) on all of the combinations of the energy bin b and the energy bin b" can be obtained. When a plurality of new energy bins are defined by integrating a plurality of energy bins, the values of g(b,i) and h(b,b",i) of the energy bins after the integration can be obtained by summing the probability of escape for each energy bin before the integration.

The probability of crosstalk is obtainable by actual measurement. The method of obtaining the value of f(b,b',i,j) by actual measurement is as follows, for example. The X-rays for which the energy distribution is known are made to enter only one of the X-ray detection elements of the X-ray detector 13. In this case, an observed count value for each energy bin of the X-ray detection element that the X-rays were not made to enter is not always zero due to crosstalk. However, when the crosstalk does not occur, the observed count value for each energy bin of the X-ray detection element that the X-rays were not made to enter is zero. Consequently, from the observed count value for each energy bin of the X-ray detection element that the X-rays were not made to enter, the values of f(b,b',i,j) on all of the combinations of the energy bin b and the energy bin b' and all of the combinations of the scintillator i and the scintillator j can be obtained. When a plurality of new energy bins are defined by integrating a plurality of energy bins, the values of f(b,b',i,j) of the energy bins after the integration can be obtained by summing the probability of escape for each energy bin before the integration.

The probability of escape is obtainable by simulation. Furthermore, the probability of crosstalk is obtainable by simulation. The method of obtaining the values of g(b,i), h(b,b",i), and f(b,b',i,j) by simulation is the one that uses the following Expression (6), for example. Expression (6) is an expression to describe a differential scattering cross-section of a photon that entered a scintillator. α in Expression (6) is expressed by the following Expression (7). Z is an effective atomic number, $r_0$ is a classical electron radius, σ is a total scattering cross-section, θ is a scattering angle, $m_0$ is a mass of an electron, ν is a vibration frequency of X-rays, c is the speed of light in vacuum, and h is Planck's constant. Expression (6) is also referred to as the Klein-Nishina formula.

$$\frac{d\sigma}{d\Omega} = Zr_0^2 \left[\frac{1}{1+\alpha(1-\cos\theta)}\right]^2 \left[\frac{1+\cos^2\theta}{2}\right]\left[1+\frac{\alpha^2(1-\cos\theta)^2}{(1+\cos^2\theta)[1+\alpha(1-\cos\theta)]}\right] \quad (6)$$

$$\alpha \cong \frac{h\nu}{m_0 c^2} \quad (7)$$

When Expression (6) is used, the ratio of a photon of X-rays having energy hν that entered one of the X-ray detection elements of the X-ray detector 13 passing through a unit solid angle in a direction of the scattering angle θ can be obtained. Consequently, by using Expression (6), the values of g(b,i) and h(b,b",i) can be obtained on all of the combinations of the energy bin b and the energy bin b', and the values of f(b,b',i,j) can be obtained on all of the combinations of the energy bin b and the energy bin b' and all of the combinations of the scintillator i and the scintillator j. The simulation using Expression (6) can be performed considering at least one of the size, shape, and position of the X-ray detection element in the X-ray detector 13.

In the foregoing, the photon-counting X-ray CT apparatus 1 in the embodiment has been explained. As in the foregoing, the correction unit 15 provided in the photon-counting X-ray CT apparatus 1 corrects, based on at least one of the probability of escape and the probability of crosstalk in the X-ray detector 13 having a plurality of X-ray detection elements, the observed count value of a photon that entered the X-ray detection element for each of a plurality of energy bins defined on the energy distribution of X-rays and for each of the X-ray detection elements. Consequently, the photon-counting X-ray CT apparatus 1 can obtain an accurate count value in which the influence of at least one of the escape and crosstalk is reduced for each of the energy bins and for each of the X-ray detection elements.

Furthermore, the correction unit 15 provided in the photon-counting X-ray CT apparatus 1 uses the result of the probability of crosstalk calculated on at least one of the other X-ray detection elements in advance when correcting the observed count value C(b,i) by using Expression (4). Consequently, the correction unit 15 can rapidly correct the observed count value based on the probability of crosstalk. Moreover, the correction unit 15 uses the result of the probability of crosstalk calculated on at least one of the other X-ray detection elements in advance in the manner described above. Consequently, the correction unit 15 can rapidly correct the observed count value.

The respective constituent elements of the devices and apparatuses illustrated in FIG. 1 are of functionally conceptual, and are not necessarily needed to be configured physically as illustrated in FIG. 1. That is, the specific embodiments of distribution or integration of the devices and apparatuses are not limited to those illustrated in FIG. 1, and the whole or a part thereof can be configured by being functionally or physically distributed or integrated in any unit according to various types of loads and usage. Furthermore, the whole or a part of the various processing functions performed in the respective devices and apparatuses is implemented by a CPU and a program executed by the CPU. Alternatively, the whole or a part of the various processing functions performed in the respective devices and apparatuses is implemented as hardware by wired logic.

The photon-counting imaging method described in the foregoing embodiment can be implemented by executing a photon-counting imaging program prepared in advance on a computer such as a personal computer and a workstation. The photon-counting imaging program can be distributed via a network such as the Internet. The photon-counting imaging program can also be recorded on a computer-readable non-transitory recording medium such as a hard disk, a flexible disk (FD), a CD-ROM, an MO, and a DVD, and executed by being read out from the recording medium by the computer.

Modified Example

Figure 8:
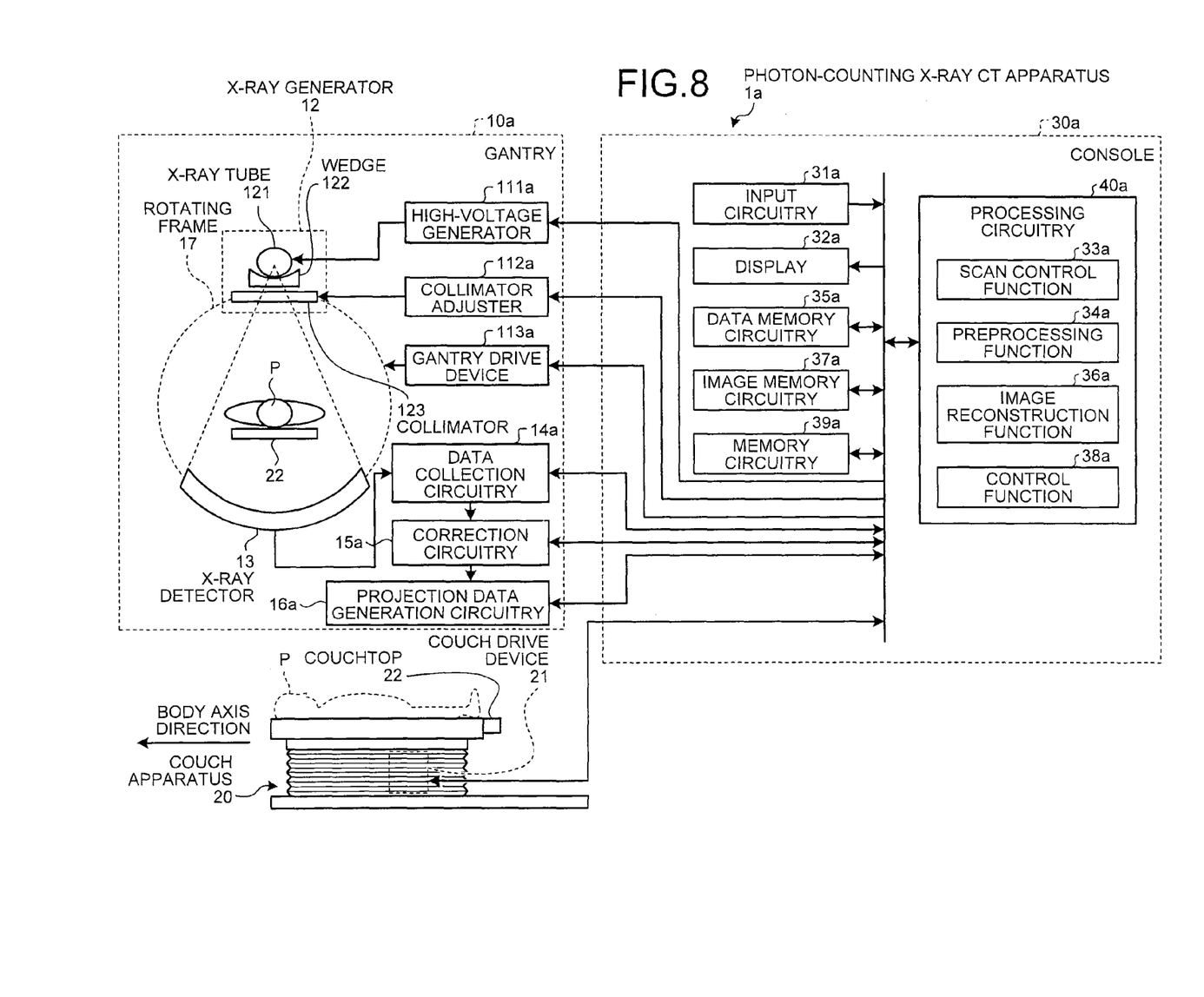
FIG. 8 is a diagram illustrating one example of the configuration of a photon-counting X-ray CT apparatus according to a modified example.

With reference to FIG. 8, the following describes a modified example of the embodiment described above. FIG. 8 is a diagram illustrating one example of the configuration of a photon-counting X-ray CT apparatus 1a according to the modified example. In regard to the same configurations as those in the embodiment described above, the same reference symbols will be used as those used in the embodiment. With respect to the content that duplicates the embodiment described above, the detailed explanations are omitted. The photon-counting X-ray CT apparatus 1a includes, as illustrated in FIG. 8, a gantry 10a, the couch apparatus 20, and an image processing apparatus 30a.

The gantry 10a irradiates the subject P with X-rays and collects projection data. The gantry 10a includes a high-voltage generator 111a, a collimator adjuster 112a, a gantry drive device 113a, the X-ray generator 12, the X-ray detector 13, data collection circuitry 14a, correction circuitry 15a, projection data generation circuitry 16a, and the rotating frame 17.

The high-voltage generator 111a supplies a tube voltage to the X-ray tube 121. The collimator adjuster 112a, by adjusting the aperture and position of the collimator 123, adjusts the irradiation range of the X-rays with which the X-ray generator 12 irradiates the subject P. The gantry drive device 113a, by rotatively driving the rotating frame 17, rotates the X-ray generator 12 and the X-ray detector 13 in a circular path centered on the subject P.

The gantry drive device 113a includes a motor, an electronic circuit, and a drive mechanism, for example. The motor generates power to rotate the rotating frame 17. The electronic circuit controls the operation of the motor. The drive mechanism transforms the power generated by the motor into the power to rotate the rotating frame 17. The drive mechanism is implemented by the combination of gears, belts, shafts, and bearings, for example.

The data collection circuitry 14a has the same function as that of the data collection unit 14 that is described in the foregoing embodiment. The data collection circuitry 14a collects the count data described above. Specifically, the data collection circuitry 14a performs such operation by reading out and executing a program stored in memory circuitry 39a, which will be described later. The data collection circuitry 14a is implemented by a processor.

The correction circuitry 15a has the same function as that of the correction unit 15 that is described in the foregoing embodiment. The correction circuitry 15a corrects a count value observed by an X-ray detection element in each of a plurality of energy bins, based on at least one of the probability of escape in the X-ray detection element and the probability of crosstalk in the X-ray detection element. The correction circuitry 15a corrects the count value for each of the X-ray detection elements. The detail of the method of correcting the count value observed by the X-ray detection element by the correction circuitry 15a is as described in the foregoing embodiment. Specifically, the correction circuitry 15a performs such operation by reading out and executing a program stored in the memory circuitry 39a described later. The correction circuitry 15a is implemented by the processor.

The projection data generation circuitry 16a has the same function as that of the projection data generator 16 that is described in the foregoing embodiment. The projection data generation circuitry 16a generates the projection data based on the count values observed by the X-ray detection elements included in the count data. Specifically, the projection data generation circuitry 16a performs such operation by reading out and executing a program stored in the memory circuitry 39a described later. The projection data generation circuitry 16a is implemented by the processor.

The image processing apparatus 30a includes input circuitry 31a, a display 32a, data memory circuitry 35a, image memory circuitry 37a, memory circuitry 39a, and processing circuitry 40a.

The input circuitry 31a is implemented with a mouse and a keyboard used by the user of the photon-counting X-ray CT apparatus 1a to input various instructions and various settings. The input circuitry 31a outputs the various instructions and various settings input by the user as an electrical signal to the processing circuitry 40a described later. The input circuitry 31a has the same function as that of the input unit 31 that is described in the foregoing embodiment. The input circuitry 31a is implemented by the processor.

The display 32a displays, based on an electrical signal received from the processing circuitry 40a described later, the result of a variety of image processing, and GUIs to receive various settings from the user via the input circuitry 31a, for example. The display 32a is a liquid crystal display or an organic electroluminescence (EL) display, for example. The display 32a has the same function as that of the display unit 32 that is described in the foregoing embodiment.

The data memory circuitry 35a stores therein raw data generated by a preprocessing function 34a, which will be described later. The data memory circuitry 35a has the same function as that of the data storage unit 35 that is described in the foregoing embodiment.

The image memory circuitry 37a stores therein CT images generated by an image reconstruction function 36a, which will be described later. The image memory circuitry 37a has the same function as that of the image storage unit 37 that is described in the foregoing embodiment.

The memory circuitry 39a stores therein respective programs to implement a scan control function 33a, the preprocessing function 34a, the image reconstruction function 36a, and a control function 38a. The memory circuitry 39a stores therein a program for the data collection circuitry 14a to implement the function of the data collection unit 14. The memory circuitry 39a stores therein a program for the correction circuitry 15a to implement the function of the correction unit 15. The memory circuitry 39a stores therein a program for the projection data generation circuitry 16a to implement the function of the projection data generator 16.

The processing circuitry 40a executes the same function as that of the scan controller 33 by reading out and executing the program corresponding to the scan control function 33a from the memory circuitry 39a. Furthermore, the processing circuitry 40a executes the same function as that of the preprocessing unit 34 by reading out and executing the program corresponding to the preprocessing function 34a from the memory circuitry 39a. The processing circuitry 40a executes the same function as that of the image reconstruction unit 36 by reading out and executing the program corresponding to the image reconstruction function 36a from the memory circuitry 39a. The processing circuitry 40a executes the same function as that of the controller 38 by reading out and executing the program corresponding to the control function 38a from the memory circuitry 39a. The processing circuitry 40a in the modified example is one example of processing circuitry specified in the appended claims. The processing circuitry 40a is implemented by the processor.

The following describes the correspondence of the modified example to the flowcharts illustrated in FIGS. 5 and 6.

The processing performed at Step S11 in FIG. 5 is implemented by the data collection circuitry 14a reading out and executing the program corresponding to the processing performed by the data collection unit 14 from the memory circuitry 39a. The processing performed at Step S12 in FIG. 5 is implemented by the correction circuitry 15a reading out and executing the program corresponding to the processing performed by the correction unit 15 from the memory circuitry 39a. That is, the processing performed at Step S1 to Step S5 in FIG. 6 is implemented by the correction circuitry 15a reading out and executing the program corresponding to the processing performed by the correction unit 15 from the memory circuitry 39a. The processing performed at Step S13 in FIG. 5 is implemented by the projection data generation circuitry 16a reading out and executing the program corresponding to the processing performed by the projection data generator 16 from the memory circuitry 39a. The processing performed at Step S14 in FIG. 5 is implemented by the processing circuitry 40a reading out and executing the program corresponding to the preprocessing function 34a from the memory circuitry 39a. The processing performed at Step S15 in FIG. 5 is implemented by the processing circuitry 40a reading out and executing the program corresponding to the image reconstruction function 36a from the memory circuitry 39a. The processing performed at Step S16 in FIG. 5 is implemented by the processing circuitry 40a reading out and executing the program corresponding to the control function 38a from the memory circuitry 39a.

The processor described above is a central processing unit (CPU), a graphics processing unit (GPU), an application specific integrated circuit (ASIC), a programmable logic device (PLD), and a field programmable gate array (FPGA), for example. The programmable logic device (PLD) is a simple programmable logic device (SPLD) and a complex programmable logic device (CPLD), for example.

The processor implements its function by reading out and executing the programs stored in the memory circuitry 39a. In the modified example described above, single processing circuitry 40a implements the scan control function 33a, the preprocessing function 34a, the image reconstruction function 36a, and the control function 38a. However, in the modified example described above, the processing circuitry 40a may be configured by combining a plurality of independent processors.

In the modified example described above, each of the scan control function 33a, the preprocessing function 34a, the image reconstruction function 36a, and the control function 38a may be implemented by independent processing circuitry. In the modified example described above, the respective independent processing circuitries that implement the scan control function 33a, the preprocessing function 34a, the image reconstruction function 36a, and the control function 38a may be integrated as desired.

Furthermore, the respective circuitries that implement the data collection circuitry 14a, the correction circuitry 15a, and the projection data generation circuitry 16a may be integrated as desired. The respective circuitries that implement the data collection circuitry 14a, the correction circuitry 15a, and the projection data generation circuitry 16a may be included in the image processing apparatus 30a.

In accordance with at least one of the embodiments in the foregoing, low noise data can be obtained.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modified examples as would fall within the scope and spirit of the inventions.

What is claimed is:

1. A photon-counting X-ray CT apparatus comprising:
    an X-ray tube configured to irradiate a subject with X-rays;
    an X-ray detector including an X-ray detection element configured to detect photons of the X-rays and to convert the photon into an electrical signal;
    data collection circuitry configured to collect a count value by counting a number of electrical signals in each of a plurality of energy bins output by the X-ray detection element;
    correction circuitry configured to determine a true count value for each X-ray detection element in each of the plurality of energy bins, based on at least one of probability of escape in the X-ray detection element and probability of crosstalk in the X-ray detection element; and
    processing circuitry configured to generate a reconstruction image, based on the true count value.

2. The photon-counting X-ray CT apparatus according to claim 1, wherein
    the energy bins include a first energy bin that includes first energy and a second energy bin that includes second energy and is lower than the first energy bin, and
    the correction circuitry is configured to determine a true count value of the first energy bin and a true count value of the second energy bin by using the determined true count value of the first energy bin.

3. The photon-counting X-ray CT apparatus according to claim 1, wherein
    the X-ray detector includes a plurality of such X-ray detection elements, and
    the correction circuitry is configured to determine a true count value for each of the X-ray detection elements.

4. The photon-counting X-ray CT apparatus according to claim 2, wherein
    the X-ray detector includes a plurality of X-ray detection elements, and
    the correction circuitry is configured to determine a true count value for each of the X-ray detection elements.

5. The photon-counting X-ray CT apparatus according to claim 3, wherein the probability of escape includes at least one of probability in which a photon having entered the X-ray detection element is not counted in an energy bin that includes energy of the photon by escape and probability in which the photon having entered the X-ray detection element is counted in one energy bin other than the energy bin that includes energy of the photon by escape.

6. The photon-counting X-ray CT apparatus according to claim 3, wherein the probability of crosstalk is probability in which a photon having entered an X-ray detection element other than the X-ray detection element a true count value of which is determined, out of the X-ray detection elements enters the X-ray detection element the true count value of which is determined, by crosstalk and is counted in an energy bin including energy the photon has at time of entering the X-ray detection element the true count value of which is determined.

7. The photon-counting X-ray CT apparatus according to claim 5, wherein the probability of crosstalk is probability in which a photon having entered an X-ray detection element other than the X-ray detection element a true count value of which is determined, out of the X-ray detection elements enters the X-ray detection element the true count value of which is determined, by crosstalk and is counted in an energy bin including energy the photon has at time of entering the X-ray detection element the true count value of which is determined.

8. The photon-counting X-ray CT apparatus according to claim 6, wherein the correction circuitry is configured to use a result of the probability of crosstalk calculated on at least one of the other X-ray detection elements in advance when determining the true count value.

9. The photon-counting X-ray CT apparatus according to claim 7, wherein the correction circuitry is configured to use a result of the probability of crosstalk calculated on at least one of the other X-ray detection elements in advance when determining the true count value.

10. The photon-counting X-ray CT apparatus according to claim 8, wherein the correction circuitry is configured to use a result of the probability of crosstalk calculated in advance on the other X-ray detection element that is in a predetermined positional relation with the X-ray detection element as the result when determining the true count value.

11. The photon-counting X-ray CT apparatus according to claim 9, wherein the correction circuitry is configured to use a result of the probability of crosstalk calculated in advance on the other X-ray detection element that is in a predetermined positional relation with the X-ray detection element as the result when determining the true count value.

12. The photon-counting X-ray CT apparatus according to claim 8, wherein the correction circuitry is configured to reduce number of other X-ray detection elements that are used for the result when determining the true count value in response to an increase in number of energy bins.

13. The photon-counting X-ray CT apparatus according to claim 9, wherein the correction circuitry is configured to reduce number of other X-ray detection elements that are used for the result when determining the true count value in response to an increase in number of energy bins.

14. The photon-counting X-ray CT apparatus according to claim 8, wherein the correction circuitry is configured to use the result on only the other X-ray detection elements for which the probability of crosstalk is equal to or higher than a predetermined threshold when determining the true count value.

15. The photon-counting X-ray CT apparatus according to claim 9, wherein the correction circuitry is configured to use the result on only the other X-ray detection elements for which the probability of crosstalk is equal to or higher than a predetermined threshold when determining the true count value.

16. The photon-counting X-ray CT apparatus according to claim 8, wherein the correction circuitry is configured to reduce number of other X-ray detection elements that are used for the result when determining the true count value in response to a decrease in a speed of correction.

17. The photon-counting X-ray CT apparatus according to claim 1, wherein at least one of the probability of escape and the probability of crosstalk is obtained by actual measurement.

18. The photon-counting X-ray CT apparatus according to claim 1, wherein at least one of the probability of escape and the probability of crosstalk is obtained by simulation.

19. The photon-counting X-ray CT apparatus according to claim 18, wherein the simulation is performed considering at least one of size, shape, and position of the X-ray detection element in the X-ray detector.

20. A photon-counting imaging method comprising:
    collecting, by data collection circuitry, a count value by counting a number of electrical signals in each of a plurality of energy bins output by X-ray detection element, the X-ray detection element being configured to detect photons of X-rays and to convert the photons into the electrical signals;
    determining, by correction circuitry, a true count value for each X-ray detection element in each of the plurality of energy bins, based on at least one of probability of escape in the X-ray detection element and probability of crosstalk in the X-ray detection element; and
    generating, by processing circuitry, a reconstruction image, based on the true count value.

\* \* \* \* \*